(12) United States Patent
Ozaki et al.

(10) Patent No.: US 12,216,695 B2
(45) Date of Patent: Feb. 4, 2025

(54) INFORMATION PROCESSING APPARATUS, INFORMATION PROCESSING METHOD, AND PROGRAM FOR ANALYZING TEXT

(71) Applicant: FUJIFILM Corporation, Tokyo (JP)

(72) Inventors: Ryota Ozaki, Tokyo (JP); Yuki Tagawa, Tokyo (JP); Norihisa Nakano, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 18/155,744

(22) Filed: Jan. 18, 2023

(65) Prior Publication Data

US 2023/0252064 A1    Aug. 10, 2023

(30) Foreign Application Priority Data

Feb. 4, 2022   (JP) ................. 2022-016653

(51) Int. Cl.
  *G06F 16/00* (2019.01)
  *G06F 16/35* (2019.01)
(52) U.S. Cl.
  CPC .................. *G06F 16/35* (2019.01)
(58) Field of Classification Search
  CPC ...... G06F 16/35; G06F 16/313; G06F 40/279; G16H 10/60; G16H 15/00; G16H 30/20; G16H 30/40; G16H 40/67
  See application file for complete search history.

(56) References Cited

U.S. PATENT DOCUMENTS

| 9,390,236 | B2 * | 7/2016 | Geller ............... G16H 15/00 |
| 9,529,898 | B2 * | 12/2016 | Epstein ............ G06F 16/353 |
| 10,180,932 | B2 * | 1/2019 | Kyre ............... G06F 40/177 |
| 10,628,476 | B2 | 4/2020 | Sohma |
| 10,878,335 | B1 * | 12/2020 | Waugh ............... G06F 40/30 |
| 11,170,892 | B1 * | 11/2021 | McKinney, IV ....... G16H 15/00 |
| 11,521,723 | B2 * | 12/2022 | Liu ............... G16H 15/00 |
| 2010/0076780 | A1 * | 3/2010 | Mahesh .............. G06Q 10/10 705/2 |
| 2014/0320677 | A1 * | 10/2014 | Jarvenpaa ............ G16H 30/40 382/128 |
| 2021/0407679 | A1 * | 12/2021 | Liu ............... G16H 40/20 |

(Continued)

FOREIGN PATENT DOCUMENTS

| JP | 2010176617 | 8/2010 |
| JP | 2016151827 | 8/2016 |

OTHER PUBLICATIONS

Jacob Devlin et al., "BERT: Pre-training of Deep Bidirectional Transformers for Language Understanding," arXiv:1810.04805v2, May 2019, pp. 1-16, Available at: https://arxiv.org/pdf/1810.04805.

*Primary Examiner* — Debbie M Le
(74) *Attorney, Agent, or Firm* — JCIPRNET

(57) ABSTRACT

Provided are an information processing apparatus, an information processing method, and a program capable of performing analysis of a text with high accuracy.

An information processing apparatus includes one or more processors and one or more memories that store a command executed by the one or more processors. The one or more processors are configured to acquire a text, classify attributes of information described in the text into a fixed unit of the text, analyze the text for each of the same classifications based on a result of the classification, and output a result of the analysis.

17 Claims, 17 Drawing Sheets

<<STEP1: ACQUIRE TEXT>>

```
COMPARE WITH 10/15.
CT <CHEST AND ABDOMEN SIMULTANEOUSLY>

IRREGULAR TUBERCLE WITH DIAMETER OF 1.5 cm IS FOUND
IN LEFT LUNG S6.
WITH INTERNAL CALCIFICATION.
BULLA IN RIGHT LUNG S3.
TUMOR WITH DIAMETER OF 6 cm IS FOUND IN LIVER S3,
ENHANCEMENT EFFECT AND washout ARE EXHIBITED,
AND HCC IS SUSPECTED.
ENHANCED TUMOR WITH DIAMETER OF 5 mm IS ALSO FOUND
IN LIVER S4 AND IS PERSISTENT.
HEMANGIOMA IS SUSPECTED.
CALCIFICATION MYOMA IN UTERUS.

PLEASE FOLLOW.
```

(56) References Cited

U.S. PATENT DOCUMENTS

2022/0270724 A1\* 8/2022 Shibata ................. H04W 12/06
2023/0170064 A1\* 6/2023 Liu ......................... G06F 40/30
705/3

\* cited by examiner

FIG. 4

```
START
  ↓
ACQUIRE INTERPRETATION REPORT — ST1
  ↓
DETERMINE TYPE OF MEDICAL PROCESS
FOR EACH SENTENCE — ST2
  ↓
DETERMINE TYPE OF ORGAN — ST3
  ↓
ANALYZE TEXT FOR EACH OF SAME
CLASSIFICATIONS TO EXTRACT TERM — ST4
  ↓
ACQUIRE RELATIONSHIP BETWEEN TERMS — ST5
  ↓
DISPLAY STRUCTURING RESULT — ST6
  ↓
END
```

FIG. 5

≪STEP1: ACQUIRE TEXT≫

COMPARE WITH 10/15.
CT <CHEST AND ABDOMEN SIMULTANEOUSLY>

IRREGULAR TUBERCLE WITH DIAMETER OF 1.5 cm IS FOUND
IN LEFT LUNG S6.
WITH INTERNAL CALCIFICATION.
BULLA IN RIGHT LUNG S3.
TUMOR WITH DIAMETER OF 6 cm IS FOUND IN LIVER S3,
ENHANCEMENT EFFECT AND washout ARE EXHIBITED,
AND HCC IS SUSPECTED.
ENHANCED TUMOR WITH DIAMETER OF 5 mm IS ALSO FOUND
IN LIVER S4 AND IS PERSISTENT.
HEMANGIOMA IS SUSPECTED.
CALCIFICATION MYOMA IN UTERUS.

PLEASE FOLLOW.

FIG. 6

《《STEP2: DETERMINE TYPE OF MEDICAL PROCESS》》

OTHER {
COMPARE WITH 10/15.
CT 〈CHEST AND ABDOMEN SIMULTANEOUSLY〉

FINDINGS/ DIAGNOSIS {
IRREGULAR TUBERCLE WITH DIAMETER OF 1.5 cm IS FOUND IN LEFT LUNG S6.
WITH INTERNAL CALCIFICATION.
BULLA IN RIGHT LUNG S3.
TUMOR WITH DIAMETER OF 6 cm IS FOUND IN LIVER S3, ENHANCEMENT EFFECT AND washout ARE EXHIBITED, AND HCC IS SUSPECTED.
ENHANCED TUMOR WITH DIAMETER OF 5 mm IS ALSO FOUND IN LIVER S4 AND IS PERSISTENT.
HEMANGIOMA IS SUSPECTED.
CALCIFICATION MYOMA IN UTERUS.

OTHER { PLEASE FOLLOW.

FIG. 7

⟨⟨STEP3: DETERMINE TYPE OF ORGAN⟩⟩

IRREGULAR TUBERCLE WITH DIAMETER OF 1.5 cm IS FOUND IN LEFT LUNG S6. WITH INTERNAL CALCIFICATION. BULLA IN RIGHT LUNG S3.
TUMOR WITH DIAMETER OF 6 cm IS FOUND IN LIVER S3. ENHANCEMENT EFFECT AND washout ARE EXHIBITED, AND HCC IS SUSPECTED.
ENHANCED TUMOR WITH DIAMETER OF 5 mm IS ALSO FOUND IN LIVER S4 AND IS PERSISTENT. HEMANGIOMA IS SUSPECTED.
CALCIFICATION MYOMA IN UTERUS.

- LUNG
- LIVER
- UTERUS

⟨⟨STEP4: EXTRACT TERM, STEP5: ACQUIRE RELATIONSHIP⟩⟩

TUMOR WITH DIAMETER OF 6 cm IS FOUND IN LIVER S3, ENHANCEMENT EFFECT AND washout ARE EXHIBITED, AND HCC IS SUSPECTED.
ENHANCED TUMOR WITH DIAMETER OF 5 mm IS ALSO FOUND IN LIVER S4 AND IS PERSISTENT. HEMANGIOMA IS SUSPECTED.

⟨⟨STEP6: DISPLAY STRUCTURING RESULT⟩⟩

| ORGAN | LOCATION | QUANTITY | LESION (+) | PROPERTY (+) | DISEASE NAME |
|---|---|---|---|---|---|
| LIVER | S3 | DIAMETER OF 6 cm | TUMOR | ENHANCEMENT EFFECT AND washout | HCC |
| LIVER | S4 | DIAMETER OF 5 mm | TUMOR | ENHANCEMENT EFFECT AND PERSISTENT | HEMANGIOMA |

PROBABILITY DISTRIBUTION FOR NER LABEL

FIG. 11

IRREGULAR TUBERCLE WITH DIAMETER OF 1.5 cm IS FOUND IN LEFT LUNG S6.
WITH INTERNAL CALCIFICATION. BULLA IN RIGHT LUNG S3.
TUMOR WITH DIAMETER OF 6 cm IS FOUND IN LIVER S3,
ENHANCEMENT EFFECT AND washout ARE EXHIBITED,
AND HCC IS SUSPECTED.

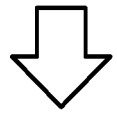

IRREGULAR TUBERCLE WITH DIAMETER
OF 1.5 cm IS FOUND IN LEFT LUNG S6./[LUNG]

WITH INTERNAL CALCIFICATION./[LUNG]

BULLA IN RIGHT LUNG S3./[LUNG]

TUMOR WITH DIAMETER OF 6 cm IS FOUND IN LIVER S3, ENHANCEMENT
EFFECT AND washout ARE EXHIBITED,
AND HCC IS SUSPECTED./[LIVER]

FIG. 12

| ORGAN | LOCATION | QUANTITY | LESION (+) | PROPERTY (+) | DISEASE NAME |
|---|---|---|---|---|---|
| LUNG | LEFT LUNG S6, RIGHT LUNG S3 | DIAMETER OF 1.5 cm | TUBERCLE, BULLA | IRREGULAR, CALCIFICATION | |
| LIVER | LIVER S3 | DIAMETER OF 6 cm | TUMOR | ENHANCEMENT EFFECT AND washout | HCC |

FIG. 13
| CYST IS FOUND IN LIVER S3 AND NO ASCITES IS FOUND. |
|---|
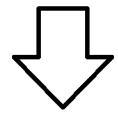
| CYST IS FOUND IN LIVER S3 AND/[LIVER] NO ASCITES IS FOUND./[ABDOMINAL CAVITY] |
|---|
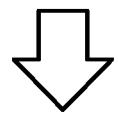
| ORGAN | LOCATION | LESION (+) |
|---|---|---|
| LIVER | LIVER S3 | CYST |
| ABDOMINAL CAVITY | | ASCITES |

FIG. 14

| ORGAN | LOCATION | QUANTITY | LESION (+) | PROPERTY (+) | DISEASE NAME |
|---|---|---|---|---|---|
| LUNG | LEFT LUNG S6 | DIAMETER OF 1.5 cm | TUBERCLE | IRREGULAR, CALCIFICATION | |
| LUNG | RIGHT LUNG S3 | | BULLA | | |
| LIVER | LIVER S3 | DIAMETER OF 6 cm | TUMOR | ENHANCEMENT EFFECT AND washout | HCC |

RIGHT CORONARY ARTERY: CALCIFICATION (+).
LEFT CORONARY ARTERY: STENOSIS (−).
IRREGULAR TUBERCLE WITH DIAMETER OF 1.5 cm IS FOUND IN LEFT LUNG S6.

RIGHT CORONARY ARTERY: CALCIFICATION (+)./[HEART]
LEFT CORONARY ARTERY: STENOSIS (−)./[HEART]
IRREGULAR TUBERCLE WITH DIAMETER OF 1.5 cm IS FOUND IN
LEFT LUNG S6./[LUNG]

| ORGAN | LOCATION | LESION (+) | LESION (−) |
|---|---|---|---|
| HEART | RIGHT CORONARY ARTERY | CALCIFICATION | |
| HEART | LEFT CORONARY ARTERY | | STENOSIS |

| ORGAN | LOCATION | QUANTITY | LESION (+) | PROPERTY (+) |
|---|---|---|---|---|
| LUNG | LEFT LUNG S6 | DIAMETER OF 1.5 cm | TUBERCLE | IRREGULAR |

FIG. 21

CHECK ERROR DISPLAY WITH AIR FLOW RATE METER.
CURRENT VALUE IS 3.8 MA WHEN CHECKED.
MALFUNCTION OF SUBSTRATE OR DIAGRAM IS CONSIDERED AFTER CONFIRMING WITH MANUFACTURER.
AIR FLOW RATE METER IS AT FAILURE FROM INVESTIGATION RESULT.
THUS, UPDATE TO SUCCESSOR MODEL IS PERFORMED.

CHECK ERROR DISPLAY WITH AIR FLOW RATE METER./[SYMPTOM]
CURRENT VALUE IS 3.8 MA WHEN CHECKED./[SYMPTOM]
MALFUNCTION OF SUBSTRATE OR DIAGRAM IS CONSIDERED AFTER CONFIRMING WITH MANUFACTURER./[CAUSE]
AIR FLOW RATE METER IS AT FAILURE FROM INVESTIGATION RESULT./[CAUSE]
THUS, UPDATE TO SUCCESSOR MODEL IS PERFORMED./[COUNTERMEASURE]

| CONTENT | PART | PHENOMENON | MEASUREMENT ITEM | MEASURED VALUE |
|---|---|---|---|---|
| SYMPTOM | AIR FLOW RATE METER | ERROR DISPLAY | CURRENT VALUE | 3.8 mA |
| CAUSE | SUBSTRATE, DIAGRAM, AND AIR FLOW RATE METER | MALFUNCTION AND FAILURE | | |
| COUNTERMEASURE | SUCCESSOR MODEL | UPDATE | | |

INFORMATION PROCESSING APPARATUS, INFORMATION PROCESSING METHOD, AND PROGRAM FOR ANALYZING TEXT

CROSS-REFERENCE TO RELATED APPLICATION

The present application claims priority under 35 U.S.C § 119 (a) to Japanese Patent Application No. 2022-016653 filed on Feb. 4, 2022, which is hereby expressly incorporated by reference, in its entirety, into the present application.

BACKGROUND OF THE INVENTION

1. Field of the Invention

The present disclosure relates to an information processing apparatus, an information processing method, and a program, and more particularly to a natural language processing technique for analyzing a text.

2. Description of the Related Art

A text created in a medical field is a text freely described by a medical worker including a doctor, and is unstructured data that is difficult to be used as it is for secondary use such as statistical analysis or content analysis. An interpretation report, which is one of medical texts, describes a result of observation by a doctor of an image captured by a medical apparatus such as a computed tomography (CT) apparatus or a magnetic resonance imaging (MRI) apparatus to grasp a location, a size, a property such as a shape or an internal structure of each disease. In order to acquire the information described in the report, there is an increasing need for a technique for structuring the text of the report.

JP2016-151827A discloses an information processing apparatus that performs analysis on a text of free description, acquires and classifies term expressions such as medical terms, and presents the classification result in a unified manner. In the information processing apparatus described in JP2016-151827A, morphological analysis and dependency analysis are used for the analysis processing, and statistical information or co-occurrence relationship is used for the classification processing.

JP2010-176617A discloses a report creation apparatus comprising a structure analysis unit that analyzes an interpretation report to identify each character string included in a text in a description unit.

SUMMARY OF THE INVENTION

Medical texts include not only a text about various organs or diseases but also a text that is not directly related to a disease, and a relationship between terms is often closed within the same organ or disease. However, in the technique of the related art, it is not possible to appropriately grasp information related to a relationship between described contents from a text including description contents related to a plurality of matters. Thus, there is a problem that a term expression cannot be accurately extracted, a medically incorrect relationship is acquired, or a necessary relationship cannot be acquired.

The present disclosure has been made in view of such circumstances, and an object of the present disclosure is to provide an information processing apparatus, an information processing method, and a program capable of performing analysis of a text with high accuracy.

An information processing apparatus according to one aspect of the present disclosure comprises one or more processors, and one or more memories that store a command executed by the one or more processors. The one or more processors are configured to acquire a text, classify attributes of information described in the text into a fixed unit of the text, analyze the text for each of the same classifications based on a result of the classification, and output a result of the analysis.

According to the present aspect, the attributes of the information described in the text are classified and the text analysis is performed within each classification. Therefore, it is possible to improve the accuracy of the analysis as compared with a case where a text in which different classifications are mixed is collectively analyzed.

In the information processing apparatus according to another aspect of the present disclosure, the fixed unit may be any one of a sentence unit, a phrase unit, a word unit, or a character unit.

In the information processing apparatus according to another aspect of the present disclosure, the text may be a medical text.

In the information processing apparatus according to another aspect of the present disclosure, a classification item of the information may include one or more of a human body part, an organ, a type of a disease, a type of a medical process, and a presence or absence of a disease. According to the present aspect, it is possible to extract medically appropriate a term expression or to acquire a medically correct relationship between terms.

In the information processing apparatus according to another aspect of the present disclosure, the type of the medical process may include at least one of findings, diagnosis, or past comparison.

In the information processing apparatus according to another aspect of the present disclosure, processing of analyzing the text for each of the same classifications may include processing of performing term extraction.

In the information processing apparatus according to another aspect of the present disclosure, processing of analyzing the text for each of the same classifications may include processing of performing term extraction and processing of acquiring a relationship between terms. According to the present aspect, it is possible to acquire a correct relationship between the terms in the text.

In the information processing apparatus according to another aspect of the present disclosure, the term extraction may include acquisition of a term expression and determination of a term type.

In the information processing apparatus according to another aspect of the present disclosure, the processing of the term extraction may be performed by using a prediction model subjected to machine learning in advance.

In the information processing apparatus according to another aspect of the present disclosure, at least one of the processing of the term extraction or the processing of acquiring the relationship between the terms may be performed by using a prediction model subjected to machine learning in advance.

In the information processing apparatus according to another aspect of the present disclosure, different prediction models may be used depending on the result of the classification.

In the information processing apparatus according to another aspect of the present disclosure, the text for each of the same classifications and classification information of the same classification may be used as an input to the prediction model.

The information processing apparatus according to another aspect of the present disclosure may further comprise an input apparatus that receives an input of the text, and a display apparatus that displays the result of the analysis.

In the information processing apparatus according to another aspect of the present disclosure, the one or more processors may be configured to save the result of the classification and perform processing of displaying the result of the classification in an identifiable manner in a case where the acquired text is displayed.

An information processing method according to another aspect of the present disclosure is an information processing method executed by one or more processors. The information processing method comprises, by the one or more processors, acquiring a text, classifying attributes of information described in the text into a fixed unit of the text, analyzing the text for each of the same classifications based on a result of the classification, and outputting a result of the analysis.

A program according to another aspect of the present disclosure causes a computer to realize a function of acquiring a text, a function of classifying attributes of information described in the text into a fixed unit of the text, a function of analyzing the text for each of the same classifications based on a result of the classification, and a function of outputting a result of the analysis.

According to the present disclosure, it is possible to improve the accuracy of the analysis of the text.

BRIEF DESCRIPTION OF THE DRAWINGS

FIG. 4 is a flowchart showing an example of an information processing method executed by the information processing apparatus.

FIG. 5 is an explanatory diagram showing an example of a text described in an interpretation report acquired by the information processing apparatus.

FIG. 6 is an explanatory diagram showing an example of a determination result in which a type of a medical process is determined in a sentence unit for the text of the interpretation report shown in FIG. 5.

FIG. 7 is an explanatory diagram showing an example of processing in which a type of an organ is determined in a sentence unit and analysis is performed on a text of the same organ.

FIG. 11 is an explanatory diagram showing an example of processing of performing organ recognition in a sentence unit.

FIG. 12 is a table showing an example of structured information obtained by performing term extraction on a sentence for each organ based on an organ recognition result shown in FIG. 11.

FIG. 13 is an explanatory diagram showing an example of processing in which the organ recognition is performed in a phrase unit and the term extraction is performed on a phrase for each organ.

FIG. 14 is a table showing an example of structured information obtained by performing the term extraction and relationship extraction on the sentence for each organ based on the organ recognition result shown in FIG. 11.

FIG. 21 is an explanatory diagram showing an example of processing of structuring a maintenance report of a factory.

DESCRIPTION OF THE PREFERRED EMBODIMENTS

Hereinafter, preferred embodiments of the present invention will be described with reference to accompanying drawings.

Configuration Example of Medical Information System

Figure 1:
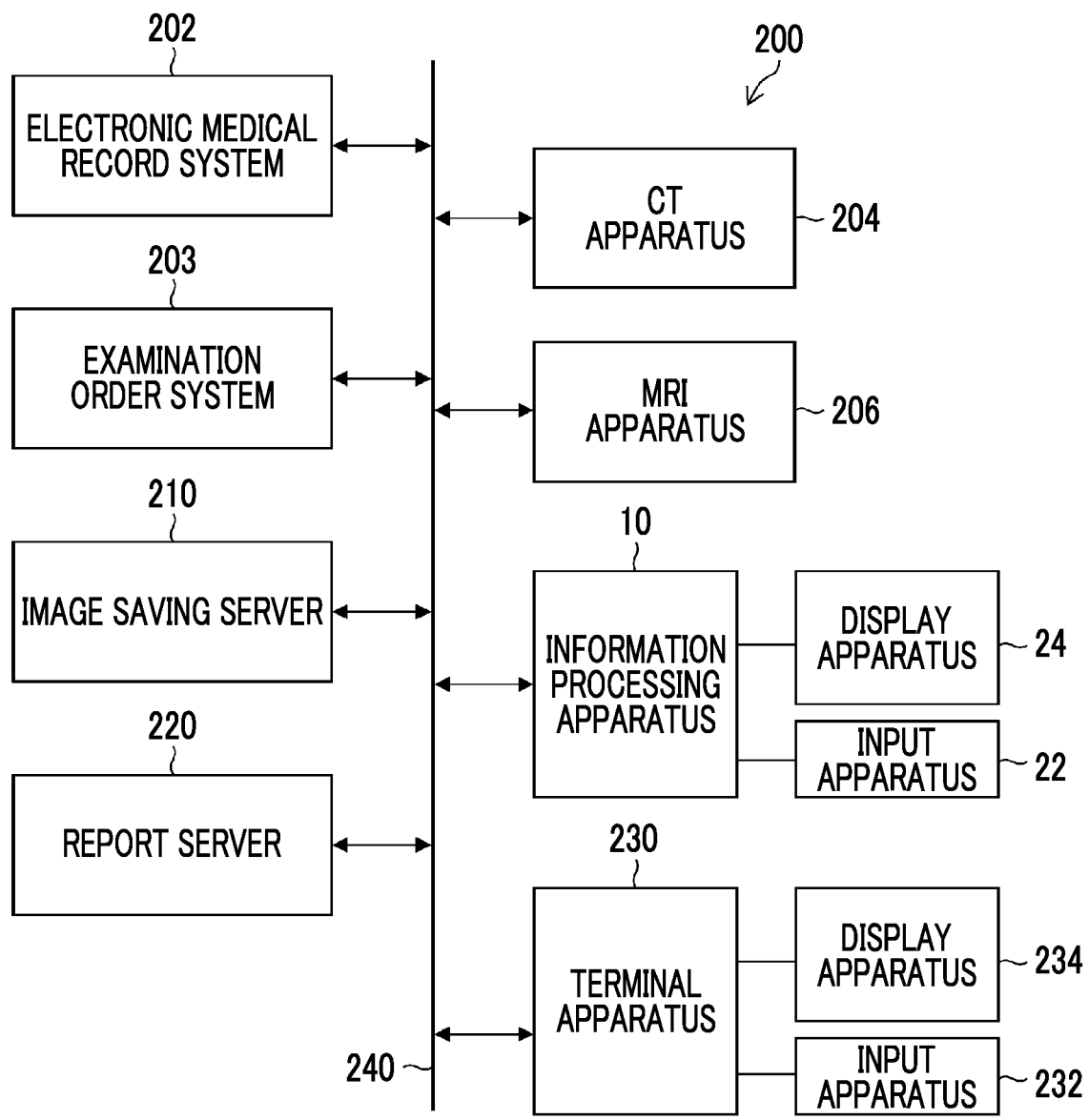
FIG. 1 is a block diagram showing a configuration example of a medical information system including an information processing apparatus according to an embodiment.

An example of an information processing apparatus 10 that analyzes a text of an interpretation report, which is a kind of a medical text, will be described. FIG. 1 is a block diagram showing a configuration example of a medical information system 200 including the information processing apparatus 10 according to an embodiment. The medical information system 200 is formed as a computer network constructed in a medical institution such as a hospital. The medical information system 200 includes an electronic medical record system 202, an examination order system 203, a CT apparatus 204, an MRI apparatus 206, an image saving server 210, a report server 220, the information processing apparatus 10, and a terminal apparatus 230, and these elements are connected via the communication line 240.

A server-type computer may be applied to each of the electronic medical record system 202 and the examination order system 203. A form in which a plurality of computers cooperate with each other may be applied to the server-type computer. The communication line 240 may be a private communication line in a medical institution. Further, a part of the communication line 240 may include a wide-area communication line. Some of the elements of the medical information system 200 may be configured by cloud computing.

In FIG. 1, the CT apparatus 204 and the MRI apparatus 206 are illustrated as examples of modalities. However, the apparatus that captures a medical image is not limited to the CT apparatus 204 and the MRI apparatus 206, and may be various examination apparatuses such as an ultrasonic diagnostic apparatus, a positron emission tomography (PET) apparatus, a mammography apparatus, an X-ray diagnostic apparatus, an X-ray fluoroscopy diagnostic apparatus, and an endoscopic apparatus (not shown). There may be various combinations of types and the number of modalities connected to the communication line 240 for each medical institution.

The electronic medical record system 202 manages an electronic medical record for each patient. The electronic medical record system 202 includes an electronic medical record storage apparatus that stores the electronic medical record. The electronic medical record system 202 may store patient identification information and the electronic medical record in association with each other and search for the electronic medical record for each patient with the patient identification information as a parameter. The electronic medical record system 202 searches for the electronic medical record in response to a readout request transmitted from the terminal apparatus 230, the information processing apparatus 10, or the like, and transmits various types of information included in the electronic medical record corresponding to the readout request to the terminal apparatus 230 or the like, which is the request source.

The examination order system 203 manages an examination order issued based on an examination order request issued by a doctor. The examination order includes various types of information related to the examination, such as the patient identification information such as a patient identification (ID), identification information of a doctor in charge of check-up such as a doctor in charge ID, and a type of examination. The examination order system 203 comprises an examination order storage apparatus that stores the examination order.

The image saving server 210 may be, for example, a digital imaging and communications in medicine (DICOM) server that operates according to a specification of DICOM. The image saving server 210 is a computer that saves and manages various types of data including images captured by using various modalities such as the CT apparatus 204 and the MRI apparatus 206, and comprises a large-capacity external storage apparatus and a program for database management. The image saving server 210 performs communication with another apparatus via the communication line 240, and transmits and receives various types of data including image data. The image saving server 210 receives various types of data including the images generated by the modality such as the CT apparatus 204 via the communication line 240, and saves and manages the received data in a recording medium such as the large-capacity external storage apparatus. A storage format of the image data and the communication between the apparatuses via the communication line 240 are based on a protocol of DICOM.

The report server 220 is a computer that saves and manages medical texts such as various reports including the interpretation report. The medical text includes a report on an image diagnosis result represented by the interpretation report, a text on the patient's medical record, and the like. In the present embodiment, the interpretation report is mainly described as an example, but a target text is not limited to the interpretation report. The description of the interpretation report can be read and understood as a text for various other purposes.

The report server 220 stores the electronic medical record, the medical image, and the interpretation report in association with each other. The report server 220 may comprise a program that supports the creation of the interpretation report. The report server 220 communicates with another apparatus via the communication line 240, and transmits and receives various types of data such as the interpretation report.

The information processing apparatus 10 can acquire data from the report server 220 and the like via the communication line 240. The information processing apparatus 10 processes text data described in the report, and performs text analysis such as classification of description information and extraction of terms. Details of processing functions of the information processing apparatus 10 will be described below. The information processing apparatus 10 can be formed by using hardware and software of a computer. The form of the information processing apparatus 10 is not particularly limited, and may be a server computer, a workstation, a personal computer, a tablet terminal, or the like. In the present embodiment, an example in which the information processing apparatus 10 and the report server 220 are separate apparatuses is described. However, a part or all of the processing functions of the information processing apparatus 10 may be incorporated into another computer such as the report server 220.

The information processing apparatus 10 may comprise an input apparatus 22 and a display apparatus 24. The input apparatus 22 may be, for example, a keyboard, a mouse, a multi-touch panel, another pointing device, a voice input apparatus, or an appropriate combination thereof. The display apparatus 24 may be, for example, a liquid crystal display, an organic electro-luminescence (OEL) display, a projector, or an appropriate combination thereof. The input apparatus 22 and the display apparatus 24 may be integrally configured as in the touch panel. The input apparatus 22 and the display apparatus 24 may be included in the information processing apparatus 10, or the information processing apparatus 10, the input apparatus 22, and the display apparatus 24 may be integrally configured.

The information processing apparatus 10 can transmit a processing result of the text analysis to other apparatuses such as the report server 220 and the terminal apparatus 230.

The terminal apparatus 230 may be a viewer terminal for image browsing, which is referred to as a picture archiving and communication systems (PACS) viewer or a DICOM viewer. Although one terminal apparatus 230 is illustrated in FIG. 1, a plurality of terminal apparatuses 230 may be connected to the communication line 240. A form of the terminal apparatus 230 is not particularly limited and may be a personal computer, a workstation, a tablet terminal, or the like. The terminal apparatus 230 comprises an input apparatus 232 and a display apparatus 234. The input apparatus 232 and the display apparatus 234 may have the same configuration as the input apparatus 22 and the display apparatus 24 of the information processing apparatus 10.

Various pieces of data saved in an image database of the image saving server 210 and various pieces of information including the processing result generated by the information processing apparatus 10 can be displayed on the display apparatus 234 of the terminal apparatus 230.

The medical information system 200 may include an image processing apparatus (not shown). The image processing apparatus comprises an image processing program that performs image analysis on the medical image captured by the modality. For example, the image processing apparatus may be configured to perform analysis processing of various computer aided diagnoses (computer aided diagnosis, computer aided detection: CAD) or the like, such as processing of recognizing a lesion region or the like from an input image, processing of specifying a classification such as a disease name, or segmentation processing of recognizing a region of an organ, or may perform processing of supporting the creation of the interpretation report using an image processing result. The processing function of the image processing apparatus may be incorporated into the information processing apparatus 10.

Outline of Processing Function of Information Processing Apparatus 10

Figure 2:
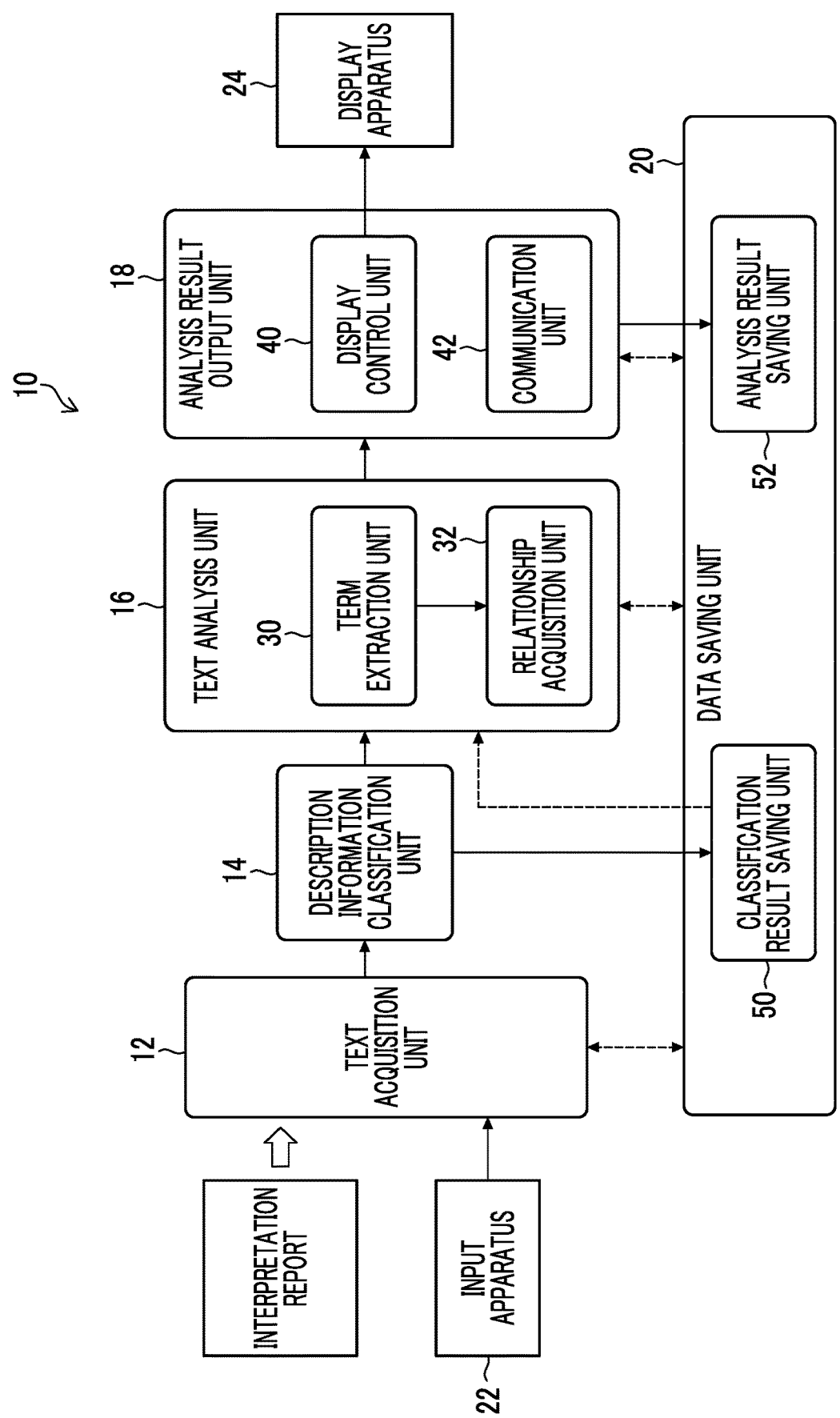
FIG. 2 is a functional block diagram showing an outline of a processing function of the information processing apparatus.

FIG. 2 is a functional block diagram showing an outline of the processing function of the information processing apparatus 10. The information processing apparatus 10 comprises a text acquisition unit 12, a description information classification unit 14, a text analysis unit 16, an analysis result output unit 18, and a data saving unit 20. The text acquisition unit 12 acquires a text to be processed. The text acquisition unit 12 may receive an input of the interpretation report saved in the report server 220 or the like, or may acquire a text input by the doctor using the input apparatus 22. Further, the text acquisition unit 12 may receive a text from another apparatus such as the terminal apparatus 230.

The text acquisition unit 12 may be configured to include a communication interface for receiving the interpretation report from an external apparatus such as the report server 220, or may be configured to include a media interface for reading the interpretation report from a removable medium such as a memory card. Further, the text acquisition unit 12 may read out the text to be processed from the data saving unit 20 in the information processing apparatus 10. The text acquisition unit 12 may be configured to include a text acquisition program for automatically acquiring the text from the data saving unit 20 or the external apparatus. The text acquired via the text acquisition unit 12 is transmitted to the description information classification unit 14. Data such as the interpretation report input from the external apparatus such as the report server 220 is saved in the data saving unit 20.

The description information classification unit 14 performs processing of classifying attributes of information described (hereinafter referred to as text description information) in a fixed unit for the input text. The fixed unit may be any unit of a sentence unit, a phrase unit, a word unit, or a character unit. The text of the interpretation report often includes a plurality of sentences, and each sentence is often a relatively short sentence. The fixed unit is preferably the sentence unit. The term "attribute" includes a concept of type. The attribute of the text description information includes, for example, one or more of a type of a human body part, a type of an organ, a type of a disease or a lesion, a type of a medical process, and the presence or absence of the disease or the lesion. The type of the medical process may include, for example, findings, diagnosis, past comparison, and message. In a case of handling the interpretation report, it is desirable that the description information classification unit 14 performs processing of classifying the type of the medical process and processing of classifying the type of the organ. A classification result by the description information classification unit 14 is saved in a classification result saving unit 50 of the data saving unit 20.

The text analysis unit 16 analyzes the text for each of the same classifications based on the classification result by the description information classification unit 14. The text analysis unit 16 includes a term extraction unit 30 and a relationship acquisition unit 32 and structures the text. The term extraction unit 30 acquires a term expression from the input text and determines a type (attribute) of each term. The relationship acquisition unit 32 acquires a relationship between the terms extracted by the term extraction unit 30. The relationship acquisition unit 32 determines whether or not there is a relationship between a subject and an object from information of a subject term, an object term, and a span between these terms in the text. Each of the term extraction unit 30 and the relationship acquisition unit 32 may be configured to use a prediction model subjected to machine learning in advance to perform the term extraction processing or the relationship acquisition processing.

The analysis result output unit 18 outputs an analysis result by the text analysis unit 16. The analysis result includes structured information indicating a structuring result. The analysis result output unit 18 converts the analysis result by the text analysis unit 16 into data in a format suitable for an output mode and outputs the data. The output mode may include display, transmission, saving, and the like. The analysis result output unit 18 may include a display control unit 40 and a communication unit 42. The display control unit 40 controls the display of the display apparatus 24. The display control unit 40 generates data for display applied to the display apparatus 24 and outputs the data for display to the display apparatus 24. Accordingly, the structured information of the analysis result is displayed on the display apparatus 24. Further, the display apparatus 24 can display the input text (unstructured text), information related to the classification result by the description information classification unit 14, and the like.

The communication unit 42 generates data for communication using the communication line 240 and transmits the data to the external apparatus such as the report server 220. Accordingly, the analysis result can be saved in the report server 220, or the analysis result can be displayed on the display apparatus 234 of the terminal apparatus 230 or the like.

Hardware Configuration Example of Information Processing Apparatus 10

Figure 3:
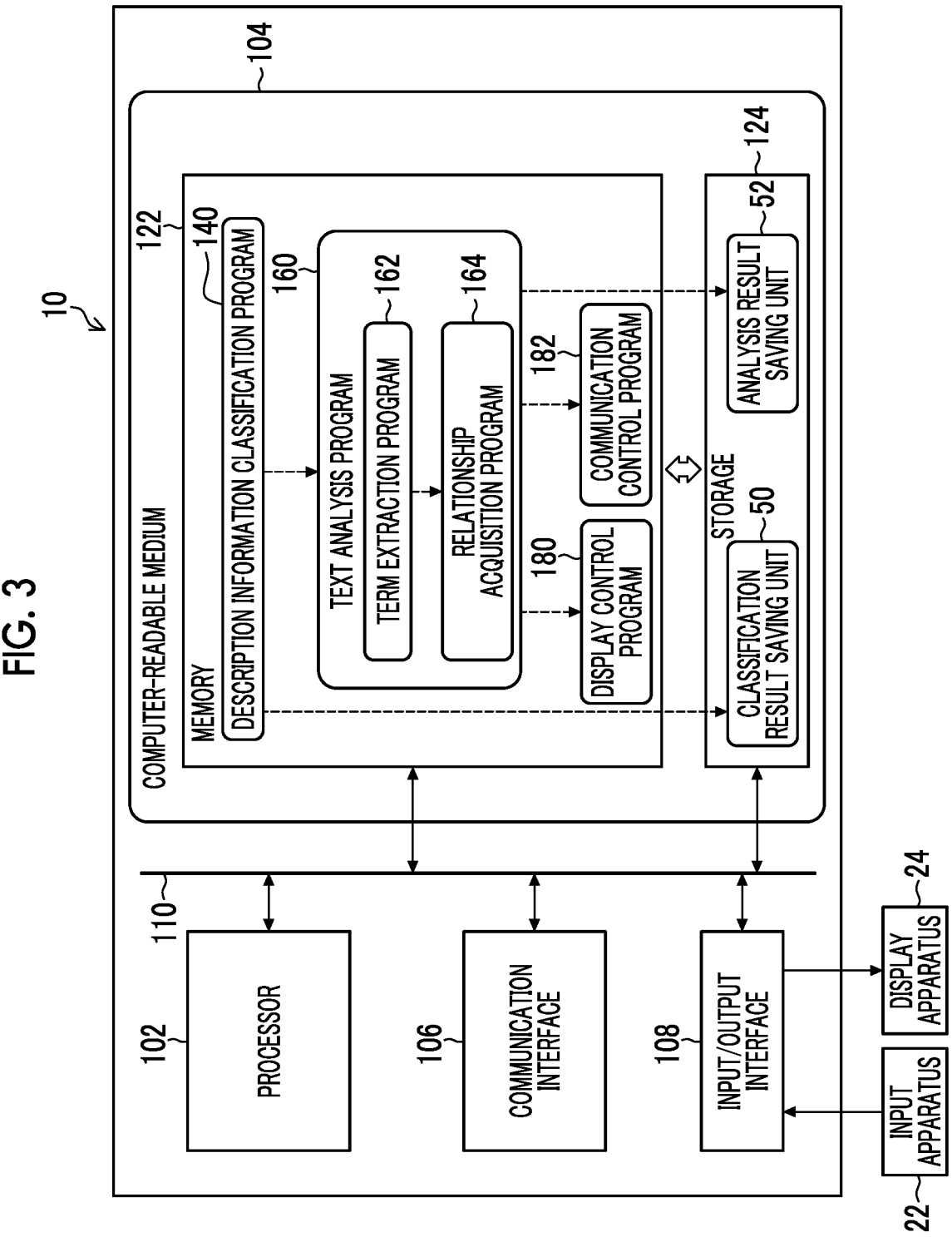
FIG. 3 is a block diagram schematically showing a hardware configuration example of the information processing apparatus.

FIG. 3 is a block diagram schematically showing a hardware configuration example of the information processing apparatus 10. The information processing apparatus 10 can be formed by a computer system configured by using one or a plurality of computers. Here, an example will be described in which one computer executes the program to realize various functions of the information processing apparatus 10.

The information processing apparatus 10 includes a processor 102, a computer-readable medium 104 that is a non-transitory tangible object, a communication interface 106, an input/output interface 108, and a bus 110.

The processor 102 includes a central processing unit (CPU). The processor 102 may include a graphics processing unit (GPU). The processor 102 is connected to the computer-readable medium 104, the communication interface 106, and the input/output interface 108 via the bus 110. The processor 102 reads out various programs, data, and the like stored in the computer-readable medium 104 to execute various types of processing. The term program includes a concept of a program module and includes a command according to the program.

The computer-readable medium 104 is, for example, a storage apparatus including a memory 122 which is a main memory and a storage 124 which is an auxiliary memory.

The storage 124 is configured by using, for example, a hard disk drive (HDD) apparatus, a solid state drive (SSD) apparatus, an optical disk, a magneto-optic disk, or a semiconductor memory, or an appropriate combination thereof. The storage 124 stores various programs, data, and the like. The storage 124 includes storage areas of the classification result saving unit 50 and an analysis result saving unit 52, and can function as the data saving unit 20 (refer to FIG. 2).

The memory 122 is used as a work area of the processor 102, and is used as a storage unit that temporarily stores the program and various types of data read out from the storage 124. The program stored in the storage 124 is loaded into the memory 122, the processor 102 executes the command of the program, and thus the processor 102 functions as a unit that performs various types of processing defined by the program. The memory 122 stores programs such as a description information classification program 140, a text analysis program 160, a display control program 180, and a communication control program 182, which are executed by the processor 102, various types of data, and the like.

The description information classification program 140 causes the processor 102 to realize the processing function as the description information classification unit 14. The text analysis program 160 causes the processor 102 to realize the processing function as the text analysis unit 16. The text analysis program 160 includes a term extraction program 162 and a relationship acquisition program 164. The term extraction program 162 and the relationship acquisition program 164 cause the processor 102 to realize the processing functions as the term extraction unit 30 and the relationship acquisition unit 32.

The display control program 180 causes the processor 102 to realize the processing function as the display control unit 40. The communication control program 182 causes the processor 102 to realize a processing function of performing the communication with the external apparatus via the communication interface 106.

The communication interface 106 performs the communication processing with the external apparatus in a wired manner or a wireless manner to exchange the information with the external apparatus. The information processing apparatus 10 is connected to the communication line 240 via the communication interface 106 (refer to FIG. 1), and can exchange the data with the apparatuses such as the image saving server 210, the report server 220, and the terminal apparatus 230. The communication interface 106 can play a role of the text acquisition unit 12 (FIG. 2) that receives the input of the text data such as the interpretation report and the communication unit 42 that outputs the analysis result.

The input apparatus 22 and the display apparatus 24 are connected to the bus 110 via the input/output interface 108.
Example of Operation of Information Processing Apparatus 10

An example of an operation of the information processing apparatus 10 will be described with reference to FIGS. 4 to 7. FIG. 4 is a flowchart showing an example of an information processing method executed by the information processing apparatus 10. In step ST1, the processor 102 receives the input of the interpretation report and acquires the interpretation report. The processor 102 can read out the interpretation report, which is an unstructured text (free description text) saved in the report server 220 or the like, and display the readout interpretation report on the display apparatus 24. FIG. 5 shows an example of a text described in the acquired interpretation report. The text shown in FIG. 5 is an example of a medical text.

Next, in step ST2 of FIG. 4, the processor 102 determines the type of the medical process for each sentence included in the acquired text. Here, an example will be shown in which the type of the medical process is classified into three types of "findings", "diagnosis", and "other". The "other" is a category in which those that do not correspond to any one of the findings or the diagnosis are classified. For example, the past comparison, the message, or the like corresponds to "other". The processor 102 determines the type of the medical process in a sentence unit and may assign a label indicating the type of the medical process to each sentence. With such labeling, each sentence is classified in terms of the type of the medical process. The determination of the type of the medical process in a sentence unit is an example of classifying the attributes of the text description information in a fixed unit. The processing of step ST2 is performed by the description information classification unit 14.

FIG. 6 shows an example of a determination result in which the type of the medical process is determined in a sentence unit for the text of the interpretation report shown in FIG. 5. As shown in FIG. 6, each sentence of a text portion of "Compare with 10/15. CT<chest and abdomen simultaneously>" is a description of "other" and is classified as "other". Each sentence of a text portion of "Irregular tubercle with diameter of 1.5 cm is found in left lung S6. With internal calcification. Bulla in right lung S3." is a description of "findings" and is classified as "findings". A sentence of "Tumor with diameter of 6 cm is found in liver S3, enhancement effect and washout are exhibited, and HCC is suspected." includes a description of "findings" and a description of "diagnosis". Thus, both a "findings" label and a "diagnosis" label may be assigned, or any one of the labels may be assigned. A sentence of "Enhanced tumor with diameter of 5 mm is also found in liver S4 and is persistent." is a description of "findings" and is classified as "findings". Each sentence of a text portion of "Hemangioma is suspected. Calcification myoma in uterus." is a description of "diagnosis" and is classified as "diagnosis". A sentence of "Please follow." is a description of the message and is classified as "other". The bulla is one of cystic lung diseases. The HCC is an abbreviation for Hepatocellular Carcinoma and means a liver cell cancer.

In a case of assuming a secondary use of the interpretation report, important description items in the text included in the interpretation report are the contents of the findings and the diagnosis, and it is desired to structure the text related to the findings and the diagnosis. Therefore, in a case where the type of the medical process is determined in a sentence unit, the processor 102 may collectively label the type of the medical process as "findings or diagnosis" without distinguishing between the "findings" and the "diagnosis". Further, the processor 102 may exclude the text classified as "other" in the texts included in the interpretation report from a target of the analysis processing by the text analysis unit 16 based on the determination (classification) result of the type of the medical process, may set the text related to the finding or the diagnosis as the target of the analysis processing by the text analysis unit 16.

Furthermore, in a case where the interpretation report, which is an unstructured text, is displayed on the display apparatus 24 or the like, the processor 102 may display the determination result (classification result) of the type of the medical process in an identifiable manner. In the example shown in FIG. 6, a display color of characters is different such as displaying characters of the text portion classified as "other" in gray and displaying characters of the text portion classified as "findings" in black. In order to relatively reduce visibility of the text portion excluded from the target of the analysis processing, various display modes may be employed such as a mode in which each group of the same classification is surrounded by a frame line, a mode in which a line feed is formed for each group of the same classification, a mode in which an annotation indicating the classification result is displayed, or an appropriate combination thereof, in addition to the mode in which the display color of the characters is different.

Next, in step ST3 of FIG. 4, the processor 102 determines the type of the organ for each sentence included in the acquired text. However, the processor 102 may exclude the sentence corresponding to "other" in the determination of the type of the medical process from the processing target of step ST3. The processor 102 determines the type of the organ in a sentence unit and classifies each sentence by the type of the organ according to the determination result. The determination of the type of the organ in a sentence unit is an example of classifying the attributes of the text description information in a fixed unit. The processing of step ST3 is performed by the description information classification unit 14.

An upper part of FIG. 7 shows an example of the result of determining the type of the organ in a sentence unit. The three sentences of "Irregular tubercle with diameter of 1.5 cm is found in left lung S6. With internal calcification. Bulla in right lung S3." are descriptions of the lung, and the type of the organ in each of these sentences is determined to be "lung". The three sentences of "Tumor with diameter of 6 cm is found in liver S3, enhancement effect and washout are exhibited, and HCC is suspected. Enhanced tumor with diameter of 5 mm is also found in liver S4 and is persistent. Hemangioma is suspected." are descriptions of the liver, and the type of the organ in each of these sentences is determined to be "liver". The sentence of "Calcification myoma in uterus." is a description of the uterus, and the type of the organ in this sentence is determined to be "uterus".

Further, in the case where the interpretation report, which is an unstructured text, is displayed on the display apparatus 24 or the like, the processor 102 displays the determination result (classification result) of the type of the organ in an identifiable manner. In the display mode in which the classification result is identifiable, various display modes may be employed such as a mode in which the display color of the characters is different for each classification, a mode in which each group of the same classification is surrounded by a frame line, a mode in which a line feed is formed for each group of the same classification, a mode in which character information indicating the classification result is displayed, or an appropriate combination thereof.

In the example shown in the upper part of FIG. 7, the display color of the characters is different such as displaying the characters of the sentence classified as "lung" in, for example, orange, displaying the characters of the sentence classified as "liver" in, for example, blue, and displaying the characters of the sentence classified as "uterus" in, for example, purple.

Next, in step ST4, the processor 102 analyzes the text for each of the same classifications based on the determination of the type of the organ to perform the term extraction. The processing of step ST4 is performed by the term extraction unit 30 of the text analysis unit 16.

In step ST5, the processor 102 acquires the relationship between the extracted terms. The processing of step ST5 is performed by the relationship acquisition unit 32 of the text analysis unit 16. The input of the type of the medical process, the type of the organ, the extracted term expression as the term expression, and the type thereof is received as the text description information, and the presence or absence of a relationship between the terms is determined to acquire the relationship. The processor 102 excludes those in which the type of the medical process is "other" and then performs the processing of acquiring the relationship in a set of sentences having the same organ type (sentence sets of the same classification).

A middle part of FIG. 7 shows an example in a case where the term extraction and the relationship acquisition are performed for the sentence classified as "liver". In the middle part of FIG. 7, a term underlined in the text is a term as the object or the subject and represents that terms connected by a broken line are related to each other. Here, it is grasped that terms of each type of a location, a quantity, a property, and a disease name related to the term "tumor", which is a term representing a lesion, are described in the text. In a case where the text is displayed, the processor 102 may display the terms extracted by the term extraction in different colors for each type.

Although not shown in FIG. 7, the pieces of processing of steps ST4 and ST5 are similarly performed for each of the sentences classified into the "lung" and the "uterus".

Next, in step ST6, the processor 102 displays the processing result of the term extraction and the relationship acquisition as a structuring result. A lower part of FIG. 7 shows a display example of the structuring result for the sentence classified as "liver".

Configuration Example of Description Information Classification Unit 14

The description information classification unit 14 can be configured by using, for example, a natural language processing model, which is referred to as bidirectional encoder representations from transformers (BERT) described in Jacob Devlin, Ming-Wei Chang, Kenton Lee, Kristina Toutanova, "BERT: Pre-training of Deep Bidirectional Transformers for Language Understanding"<https://arxiv.org/pdf/1810.04805>. The present invention is not limited to BERT, and another machine learning model such as a recurrent neural network (RNN) or a support vector machine (SVM) may be applied.

The description information classification unit 14 determines what is written about the input text in a fixed unit, for example, in a sentence unit, by using a text classification technique. In a case where a text includes a plurality of sentences, the description information classification unit 14 determines which classification each sentence belongs to from connection of each sentence in the text.

In a case where the text is structured for each organ, the description information classification unit 14 determines the type of the organ of each sentence in the report by using the text classification technique. In a case where a text is input to the description information classification unit 14, a sentence surrounding a target sentence may also be input to determine the type of the organ. The surrounding sentence may be an N sentence before the target sentence and an M sentence after the target sentence. N represents an integer of 1 or more and M represents an integer of 0 or more. For example, in a case where the target sentence is the text of "With internal calcification" in the text of "Irregular tubercle with diameter of 1.5 cm is found in left lung S6. With internal calcification.", the two sentences of "Irregular tubercle with diameter of 1.5 cm is found in left lung S6. With internal calcification." are input including the previous sentence as an input to the BERT model. With the input of the two sentences, it is possible to determine that the target sentence is a sentence related to "lung".

Configuration Example of Term Extraction Unit 30

The term extraction unit 30 uses a named entity recognition (NER) technique to acquire the term expression and determine the type thereof. A task of the term extraction unit 30 includes a classification task of receiving an input of a token series and predicting a label for each token being input, and a task of distinguishing between a start and an end of a named entity (NE) by a BIO method. In the BIO method, the start and the end of the named entity are grasped by using tags of "Begin" indicating the start of the named entity, "Inside" indicating a continuation (inside) of the named entity, and "other" indicating something that is not the named entity (other than named entity).

Figure 8:
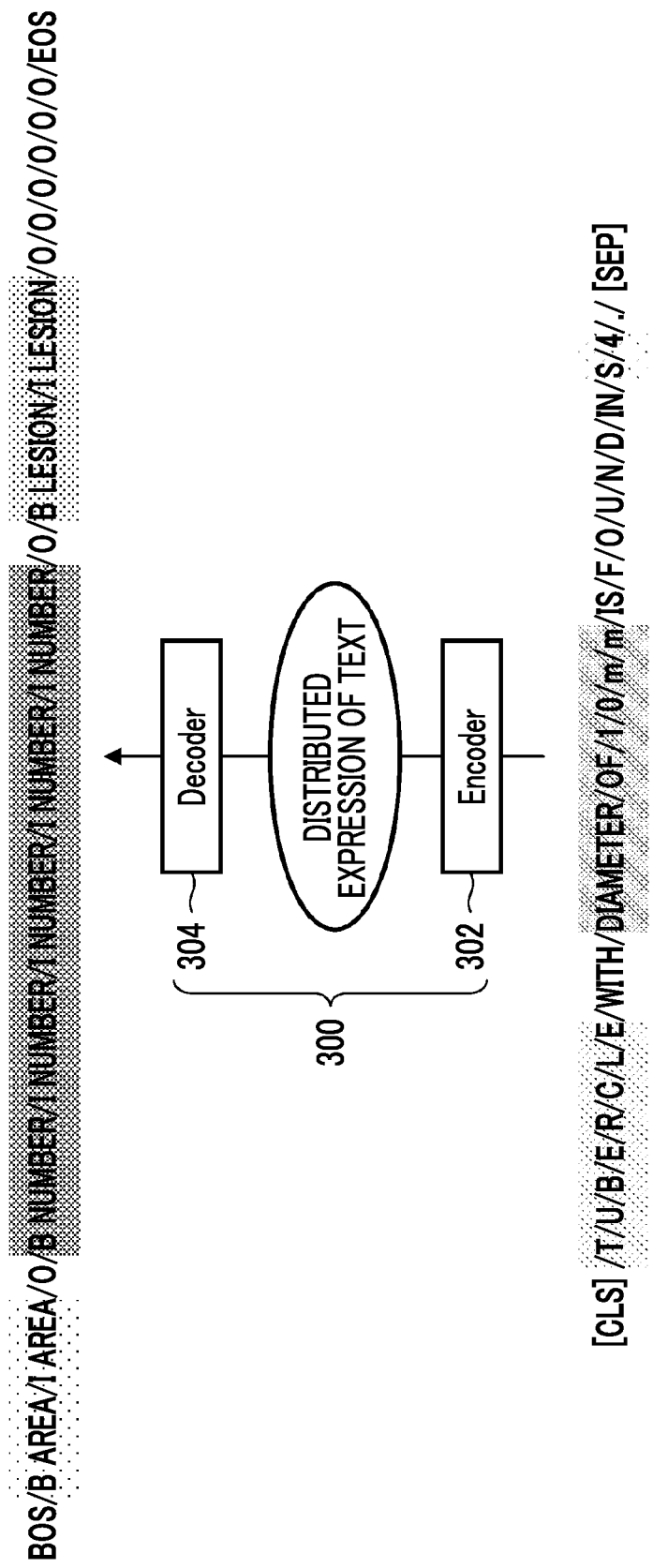
FIG. 8 is an explanatory diagram showing a configuration example of a term extraction unit in the information processing apparatus.

The term extraction unit 30 can be configured using, for example, an encoder-decoder model. FIG. 8 shows an example of a term extraction model 300 applied to the term extraction unit 30. The term extraction model 300 includes an encoder 302 and a decoder 304. The encoder 302 is configured by using, for example, a neural network such as BERT or long short term memory (LSTM). The encoder 302 obtains a distributed expression from an input text. The decoder 304 predicts a probability distribution for the label from the distributed expression of each token output from the encoder 302 by a fully-connected layer. In the NER, an NER label in which a BIO label is combined with an NE label is handled.

For example, a label "B area" shown in FIG. 8 is an NER label in which "Begin" of the BIO label is combined with "Area" of the NE label. A label "I lesion" is an NER label in which "Inside" of the BIO label is combined with "Lesion" of the NE label.

Figure 9:
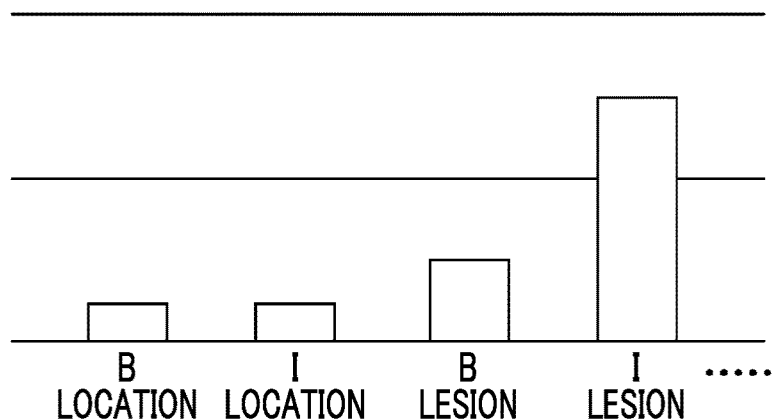
FIG. 9 is a graph showing an example of a probability distribution for a named entity recognition (NER) label.

FIG. 9 shows an example of the probability distribution of the NER label obtained by the decoder 304. The term extraction model 300 is trained to minimize cross-entropy of a softmax function output of the decoder 304.

Configuration Example of Relationship Acquisition Unit 32

Figure 10:
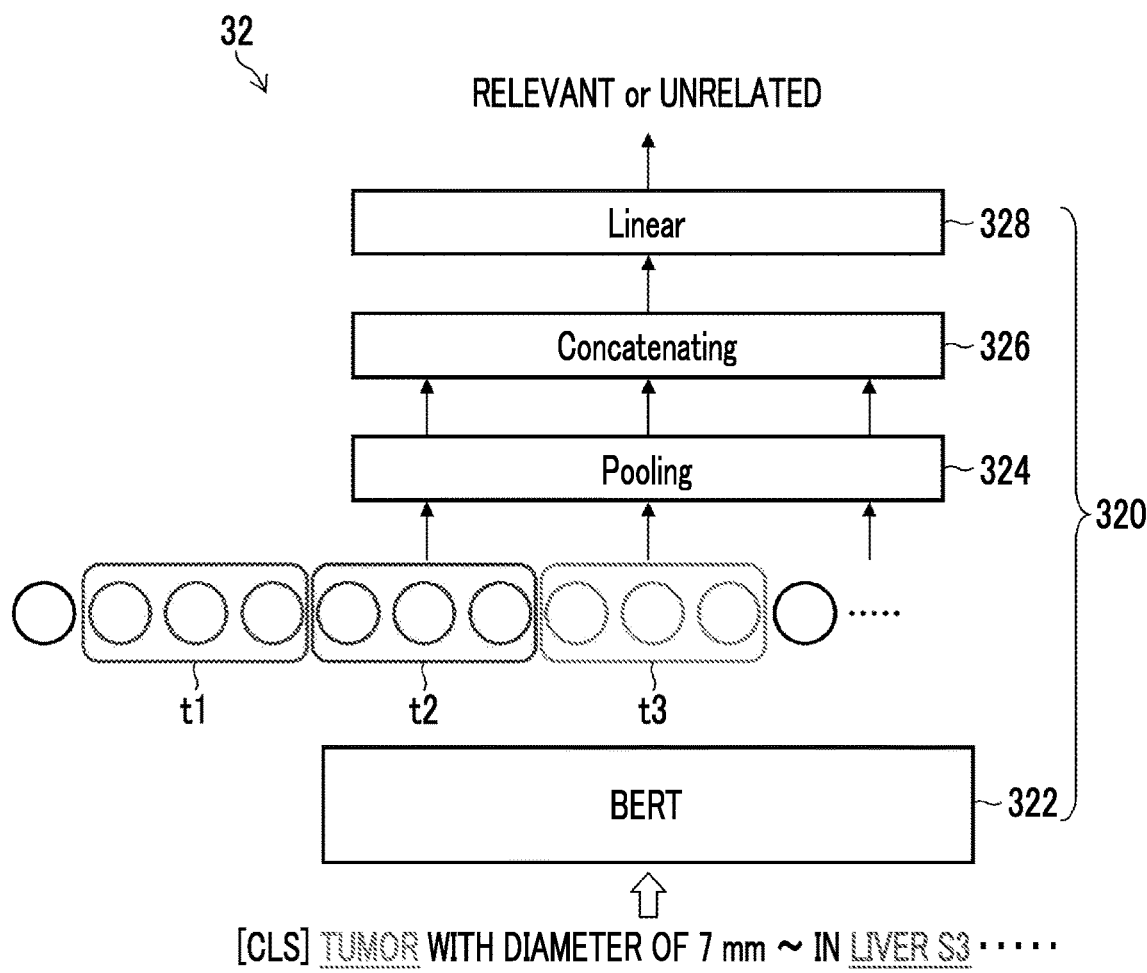
FIG. 10 is an explanatory diagram showing a configuration example of a relationship acquisition unit in the information processing apparatus.

FIG. 10 is a block diagram showing a configuration example of the relationship acquisition unit 32. The relationship acquisition model 320 applied to the relationship acquisition unit 32 has, for example, a structure in which a pooling layer 324, a concatenating layer 326, and a linear layer 328 are added to an output of a BERT model 322.

The relationship acquisition unit 32 performs binary classification of the presence or absence of the relationship for the input text from the subject term, the object term, and the span between these terms.

In the input text illustrated in FIG. 10, the term "liver S3" is the subject term, the term "tumor" is the object term, and a character string of "with diameter of 7 mm" between these terms is the span. In a case where a text is input to the BERT model 322, output values t1, t2, t3, . . . , and the like for each token are obtained from the BERT model 322. In FIG. 10, "000" surrounded by a square with rounded corners represents an output value corresponding to each token. For example, the output value t1 in FIG. 10 represents an output value corresponding to the token of "liver S3" in an input token string. The output value t2 represents an output value corresponding to the token of the span, and the output value t3 represents an output value corresponding to the "tumor".

The output of the BERT model 322 is input to the pooling layer 324 and is subjected to pooling processing by the pooling layer 324. An output of the pooling layer 324 is input to the concatenating layer 326 and is subjected to concatenating processing by the concatenating layer 326. An output of the concatenating layer 326 is subjected to linear conversion processing by the linear layer 328. Binarization indicating "relevant" or "unrelated" is performed based on a value output from the linear layer 328.

Various Application Examples

The configuration has been described in which the above information processing apparatus 10 performs the text analysis for each of the same classifications to perform the term extraction and the relationship acquisition. However, a configuration may be employed in which only the term extraction is performed as the processing content of the text analysis performed for each of the same classifications. Further, the classification is not limited to the sentence unit and may be the phrase unit or the like. Hereinafter, specific variations of application examples will be described as Examples 1 to 7.

Example 1

Example 1 is an example in which an organ recognition result in a sentence unit is used to perform the term extraction on the sentence for each organ for the structuring. An upper part of FIG. 11 shows an example of structuring the medical text of "Irregular tubercle with diameter of 1.5 cm is found in left lung S6. With internal calcification. Bulla in right lung S3. Tumor with diameter of 6 cm is found in liver S3, enhancement effect and washout are exhibited, and HCC is suspected".

In this case, the processor 102 performs organ recognition for each sentence from the first sentence to the fourth sentence to obtain a result of "lung, lung, lung, liver". A notation of the organ recognition result of "lung, lung, lung, liver" means a classification result that each of the first sentence to the third sentence is a sentence related to the lung and the fourth sentence is a sentence related to the liver. In a lower part of FIG. 11, the result of the organ recognition for each sentence is shown by a notation such as "/[lung]".

The processor 102 performs the term extraction on the sentence for each organ based on the classification result of each sentence and thus can obtain structured information of "organ: lung, location: left lung S6 and right lung S3, quantity: diameter of 1.5 cm, lesion (+): tubercle and bulla, property (+): irregular, calcification" and "organ: liver, location: liver S3, quantity: diameter of 6 cm, lesion (+): tumor, property (+): enhancement effect and washout, disease name: HCC" as shown in FIG. 12. The type of the lesion and the disease name, such as tubercle, bulla, or HCC, are examples of the type of the disease.

Example 2

Example 2 is an example in which an organ recognition result in a phrase unit is used to perform the term extraction on the phrase for each organ for the structuring. An upper part of FIG. 13 shows an example of structuring a medical text of "Cyst is found in liver S3 and no ascites is found". The processor 102 performs the organ recognition on each phrase of this sentence to obtain a classification result that "Cyst is found in liver S3" is the liver and "no ascites is found" is the abdominal cavity. In a middle part of FIG. 13, the result of organ recognition for each phrase is shown by a notation such as "/[liver]".

The processor 102 performs the term extraction on the phrase for each organ and thus can obtain structured information of "organ: liver, location: liver S3, lesion (+): cyst" and "organ: abdominal cavity, lesion (−): ascites" as shown in a lower part of FIG. 13.

Example 3

Example 3 is an example in which the organ recognition result in a sentence unit is used to perform the term extraction and the relationship acquisition on the sentence for each organ for the structuring. As in Example 1, an example will be described in which the medical text of "Irregular tubercle with diameter of 1.5 cm is found in left lung S6. With internal calcification. Bulla in right lung S3. Tumor with diameter of 6 cm is found in liver S3, enhancement effect and washout are exhibited, and HCC is suspected." is structured.

The processor 102 performs the organ recognition for each sentence to obtain a result of "lung, lung, lung, liver". The processor 102 performs the term extraction and the relationship acquisition on the sentence for each organ and thus can obtain structured information of "organ: lung, location: left lung S6, quantity: diameter of 1.5 cm, lesion (+): tubercle, property (+): irregular and calcification", "organ: lung, location: right lung S3, lesion (+): bulla", and "organ: liver, location: liver S3, quantity: diameter of 6 cm, lesion (+): tumor, property (+): enhancement effect and washout, disease name: HCC" as shown in FIG. 14. As another form, in a case where a model is used in which the sentence for each organ and the type of the organ can be considered, a configuration may be employed in which the type of the organ is input to the model in addition to the sentence for each organ to perform the term extraction or the relationship acquisition.

Example 4

Figure 15:
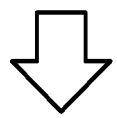
FIG. 15 is an explanatory diagram showing an example of processing in which the organ recognition is performed in a sentence unit and text analysis is performed on a sentence for each organ by using a model different for each organ.

Example 4 is an example in which the organ recognition result in a sentence unit is used to perform the term extraction and the relationship acquisition, using a different model for each organ, on the sentence for each organ for the structuring. An upper part of FIG. 15 shows an example of structuring a medical text of "Right coronary artery: calcification (+). Left coronary artery: stenosis (−). Irregular tubercle with diameter of 1.5 cm is found in left lung S6".

The processor 102 performs the organ recognition on each sentence to obtain a classification result of "heart, heart, lung". In a lower part of FIG. 15, the result of organ recognition for each sentence is shown by a notation such as "/[heart]".

Based on the result of such organ recognition, the processor 102 uses a machine learning model trained for the heart for the sentence described for the heart and uses a machine learning model trained for the lung for the sentence described for the lung to perform the term extraction and the relationship acquisition.

Figure 16:
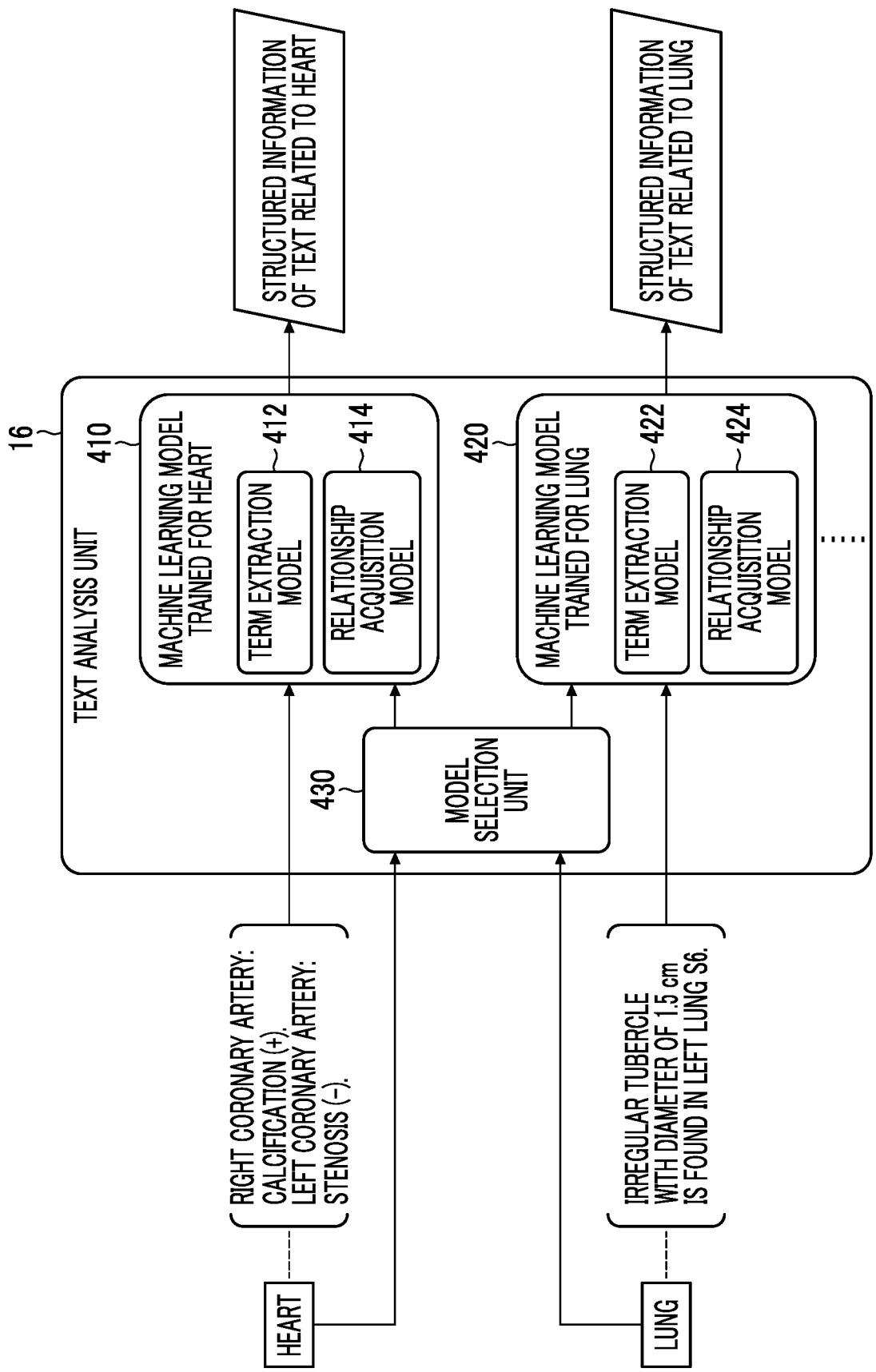
FIG. 16 is a block diagram showing a configuration example of a text analysis unit using a model different for each organ.

FIG. 16 is a conceptual diagram of the text analysis unit 16 applied to Example 4. The text analysis unit 16 shown in FIG. 16 includes a machine learning model 410 trained for the heart, a machine learning model 420 trained for the lung, and a model selection unit 430 that selects a model to be used. The machine learning model 410 trained for the heart is a learned model trained using a text describing the heart as learning data, and includes a term extraction model 412 trained to perform a term extraction task and a relationship acquisition model 414 trained to perform a relationship acquisition task.

The machine learning model 420 trained for the lung is a learned model trained using a text described about the lung as learning data, and includes a term extraction model 422 trained to perform the term extraction task and a relationship acquisition model 424 trained to perform the relationship acquisition task. Although not shown in FIG. 16, the text analysis unit 16 may include a model trained for another organ, such as a machine learning model trained for the liver.

The model selection unit 430 performs processing of selectively switching the machine learning model to be used based on the classification information obtained as a result of the organ recognition. For example, in a case where the classification information of the input text indicates a label of "heart", the model selection unit 430 selects the machine learning model 410 trained for the heart as the model used for the text analysis. The term extraction and the relationship acquisition are performed on the text related to the heart using the machine learning model 410 trained for the heart to obtain the structured information of the text related to the heart. Further, in a case where the classification information of the input text indicates a label of "lung", the model selection unit 430 selects the machine learning model 420 trained for the lung as the model used for the text analysis. The term extraction and the relationship acquisition are performed on the text related to the lung using the machine learning model 420 trained for the lung to obtain the structured information of the text related to the lung.

Figures 17, 18, 19:
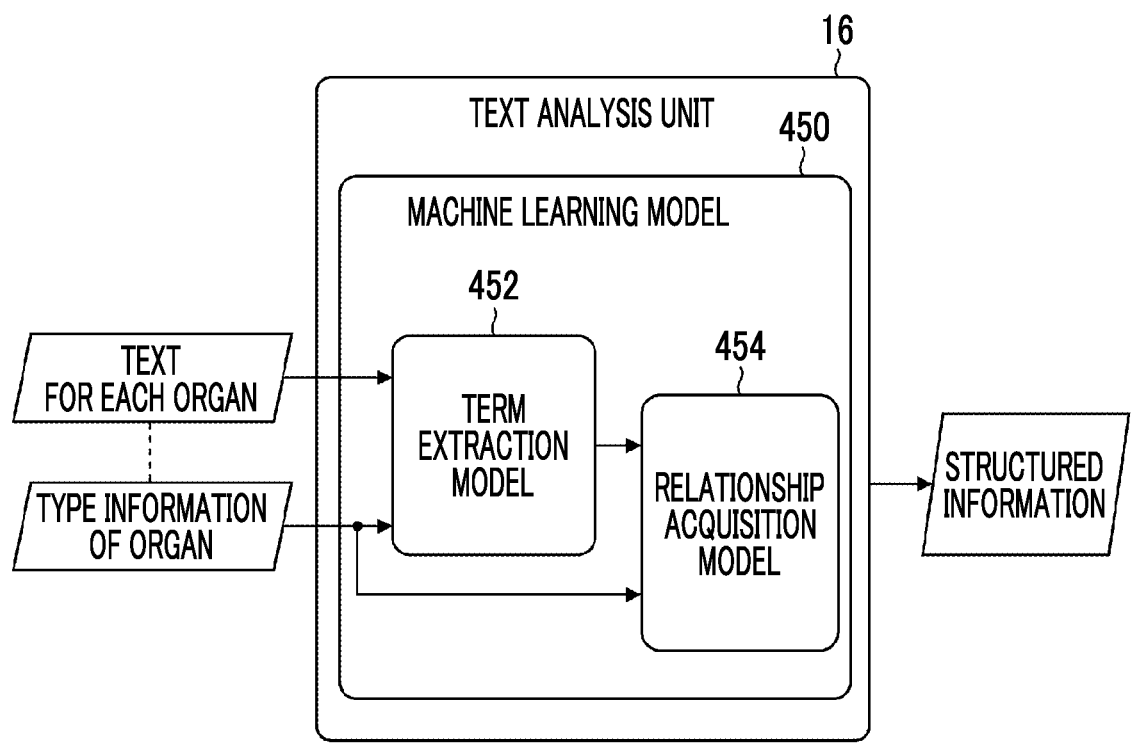
FIG. 17 is a table showing an example of structured information obtained by text analysis using a machine learning model trained for the heart shown in FIG. 16.
FIG. 18 is a table showing an example of structured information obtained by the text analysis using a machine learning model trained for the lung shown in FIG. 16.
FIG. 19 is a conceptual diagram of the text analysis unit using a model in which the organ recognition result is input as auxiliary information.

FIG. 17 is an example of structured information obtained by the text analysis using the machine learning model 410 trained for the heart. FIG. 18 is an example of structured information obtained by the text analysis using the machine learning model 420 trained for the lung.

As described with reference to FIG. 16, with the text analysis using an appropriate model in accordance with the type of the organ, it is possible to perform more accurate analysis. With such a configuration, it is possible to perform the structuring with high accuracy even in a case where the writing is different depending on the organ and to obtain structured information of "organ: heart, location: right coronary artery, lesion (+): calcification", "organ: heart, location: left coronary artery, lesion (−): stenosis", and "organ: lung, location: left lung S6, quantity: diameter of 1.5 cm, lesion (+): tubercle, property (+): irregular" as shown in FIGS. 17 and 18.

The present invention is not limited to the configuration in which the machine learning model is individually prepared for each organ. For example, a mode may be employed in which the machine learning model 410 trained for the heart is prepared for an organ with a special text expression, for example, the heart and a machine learning model trained for an organ other than the heart is employed for the organ other than the heart.

Example 5

Example 5 is an example referred to as another form of Example 3 and is an example in which a model in which the organ recognition result is input as auxiliary information is used in a case where the organ recognition result in a sentence unit is used to perform the term extraction and the relationship acquisition on the sentence for each organ.

FIG. 19 is a conceptual diagram of the text analysis unit 16 applied to Example 5. The text analysis unit 16 shown in FIG. 19 includes a machine learning model 450 that processes the text related to various organs. The machine learning model 450 includes a term extraction model 452 that performs the term extraction task and a relationship acquisition model 454 that performs the relationship acquisition task. The text for each organ and type information (classification information) of the organ indicating the organ recognition result of the text are input to the machine learning model 450. With the input of the classification information of the organ as the auxiliary information, each of the term extraction model 452 and the relationship acquisition model 454 can perform the term extraction and the relationship acquisition with high accuracy.

In a case where the machine learning model 450 commonly used for the text related to the various organs is trained, data including the text related to the various organs and the type information of the organ indicating the classification of the text is used as the learning data.

Figure 20:
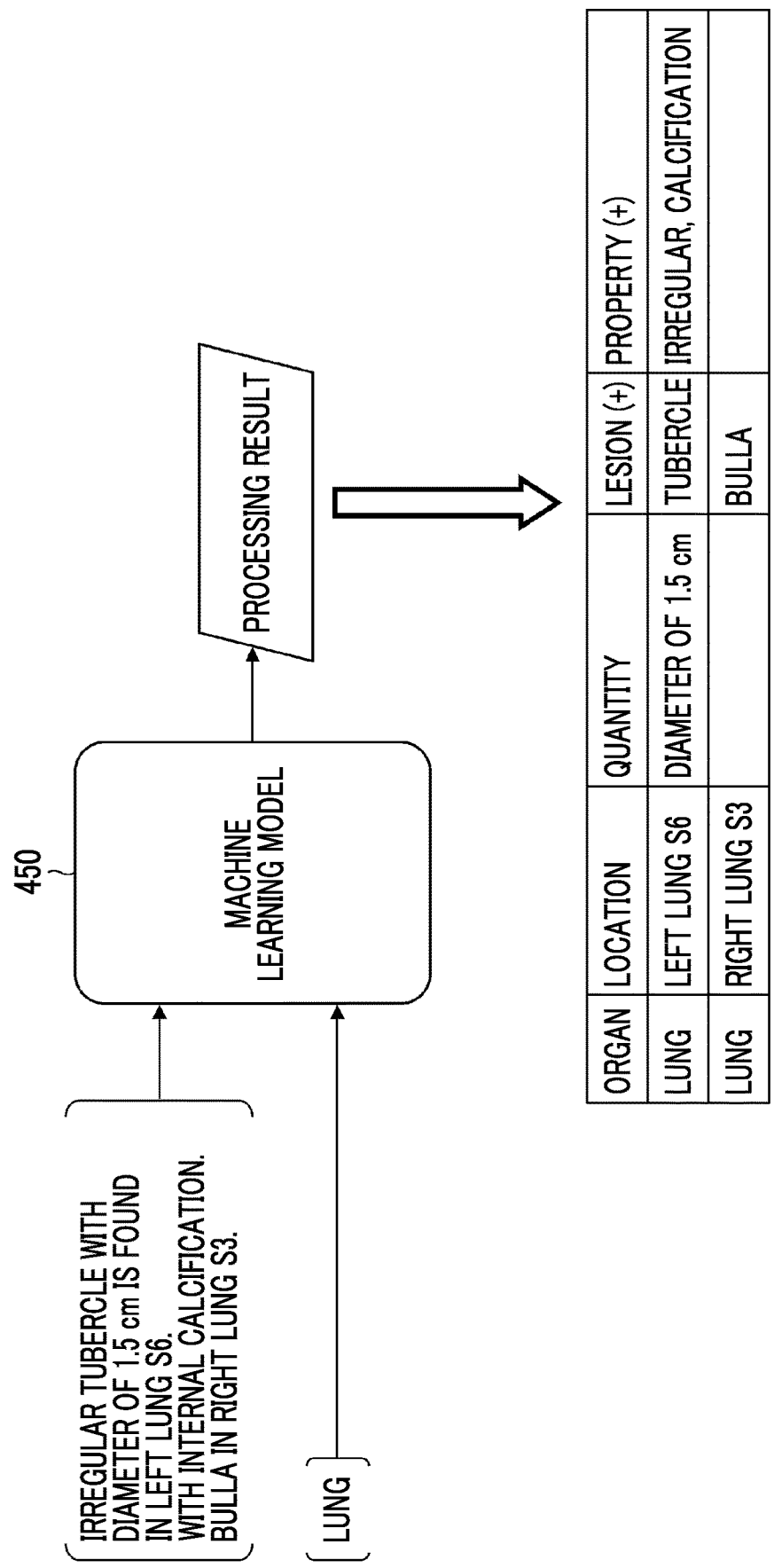
FIG. 20 is an explanatory diagram showing an example of processing by the machine learning model shown in FIG. 19.

FIG. 20 is an explanatory diagram showing an example of the processing by the machine learning model 450. As shown in FIG. 20, for example, the text of "Irregular tubercle with diameter of 1.5 cm is found in left lung S6. With internal calcification. Bulla in right lung S3." and the auxiliary information of "lung" indicating the type of the organ is input to the machine learning model 450, and an output of a processing result is obtained from the machine learning model 450. From the processing result of the machine learning model 450, structured information of "organ: lung, location: left lung S6, quantity: diameter of 1.5 cm, lesion (+): tubercle, property (+): irregular, calcification" and "organ: lung, location: right lung S3, lesion (+): bulla" is obtained.

Example 6

The information processing apparatus 10 that handles the interpretation report has been described so far. However, the technique of the present disclosure is not limited to an image diagnosis report represented by the interpretation report, but is applicable to a system that handles various medical texts such as a text related to the patient's medical record. The text related to the patient's medical record includes, for example, an intermediate summary or a discharge summary. Further, the technique of the present disclosure is not limited to medical text, but is applicable to processing that handles texts in various fields, such as a factory maintenance report, an examination result report of an industrial product, an examination result report of a building or the like, or various types of appraisal reports, regardless of a type of an object or use.

In Example 6, an example of handling the maintenance report of the factory will be described. FIG. 21 is an example of processing of structuring by classifying the maintenance report of the factory into the types of contents in a sentence unit and performing the term extraction for each of the same classifications. An upper part of FIG. 21 shows an example of structuring a maintenance report of "Check error display with air flow rate meter. Current value is 3.8 mA when checked. Malfunction of substrate or diagram is considered after confirming with manufacturer. Air flow rate meter is at failure from investigation result. Thus, update to successor model is performed".

The information processing apparatus that processes such a text may be configured to be the same as the configuration of the information processing apparatus 10 described with reference to FIG. 2 or is configured to perform determination as to whether each sentence is "symptom", "cause", or "countermeasure", instead of the determination of the type of the organ. In this case, a result of "symptom, symptom, cause, cause, countermeasure" is obtained as shown in a middle part of FIG. 21 as a classification result of each sentence by the description information classification unit 14.

The text analysis unit 16 performs the term extraction on the sentences for each of the classified contents. Accordingly, it is possible to obtain structured information of "content: symptom, part: air flow rate meter, phenomenon: error display, measurement item: current value, measured value: 3.8 mA", "content: cause, part: substrate, diagram, and air flow rate meter, phenomenon: malfunction and failure", and "content: countermeasure, part: successor model, phenomenon: update" as shown in a lower part of FIG. 21.

Program for Operating Computer

A program causing a computer to realize a part or all of the processing functions in the above information processing apparatus 10 can be recorded on a computer-readable medium which is a non-transitory tangible information storage medium such as an optical disk, a magnetic disk, or a semiconductor memory, and the program can be provided through this information storage medium.

Further, instead of the mode in which the program is provided by being stored in such a non-transitory tangible computer-readable medium, a program signal may be provided as a download service using a telecommunication line such as the Internet.

Furthermore, a part or all of the processing functions in the information processing apparatus 10 may be realized by cloud computing, or may be provided as a software as a service (SasS).

Hardware Configuration of Each Processing Unit

A hardware structure of the processing units executing various types of processing such as the text acquisition unit 12, the description information classification unit 14, the text analysis unit 16, the analysis result output unit 18, the term extraction unit 30, the relationship acquisition unit 32, and the display control unit 40 in the information processing apparatus 10 is, for example, various processors as shown below.

The various processors include a CPU which is a general-purpose processor that functions as various processing units by executing a program, a GPU which is a processor specialized for image processing, a programmable logic device (PLD) such as a field programmable gate array (FPGA) which is a processor capable of changing a circuit configuration after manufacture, a dedicated electric circuit such as an application specific integrated circuit (ASIC) which is a processor having a circuit configuration specifically designed to execute specific processing, and the like.

One processing unit may be configured by one of these various processors or may be configured by two or more processors having the same type or different types. For example, one processing unit may be configured by a plurality of FPGAs, a combination of a CPU and an FPGA, or a combination of a CPU and a GPU. The plurality of processing units may be configured of one processor. As an example in which the plurality of processing units are configured by one processor, firstly, as represented by a computer such as a client and a server, a form may be employed in which one processor is configured by a combination of one or more CPUs and software and the processor functions as the plurality of processing units. Secondly, as represented by a system on chip (SoC) or the like, a form may be employed in which a processor that realizes the function of the entire system including the plurality of processing units by one integrated circuit (IC) chip is used. As described above, the various processing units are configured by using one or more various processors as a hardware structure.

Further, as the hardware structure of the various processors, more specifically, an electric circuit (circuitry) in which circuit elements such as semiconductor elements are combined may be used.

Advantages According to Embodiment

With the information processing apparatus 10 according to the present embodiment, the analysis processing such as the term extraction is performed for each text belonging to the same classification. Therefore, it is possible to analyze the text with high accuracy and to acquire a correct relationship between the terms in the text. Accordingly, it is possible to obtain the structured information with high accuracy. The technique of the present disclosure is particularly effective in a case of analyzing a text including a plurality of sentences describing a plurality of matters having different types (attributes).

Other

The present disclosure is not limited to the above embodiment, and various modifications can be made without departing from the spirit of the technical idea of the present disclosure.

EXPLANATION OF REFERENCES

10: information processing apparatus
12: text acquisition unit
14: description information classification unit
16: text analysis unit
18: analysis result output unit
20: data saving unit
22: input apparatus
24: display apparatus
30: term extraction unit
32: relationship acquisition unit
40: display control unit
42: communication unit
50: classification result saving unit
52: analysis result saving unit
102: processor
104: computer-readable medium
106: communication interface
108: input/output interface
110: bus
122: memory
124: storage
140: description information classification program
160: text analysis program
162: term extraction program
164: relationship acquisition program
180: display control program
182: communication control program
200: medical information system
202: electronic medical record system
203: examination order system
204: CT apparatus
206: MRI apparatus
210: image saving server
220: report server
230: terminal apparatus
232: input apparatus
234: display apparatus
240: communication line
300: term extraction model
302: encoder
304: decoder
320: relationship acquisition model
322: BERT model
324: pooling layer
326: concatenating layer
328: linear layer
410: machine learning model
412: term extraction model
414: relationship acquisition model
420: machine learning model
422: term extraction model
424: relationship acquisition model
430: model selection unit
450: machine learning model
452: term extraction model
454: relationship acquisition model
ST1~ST6: step of information processing method

What is claimed is:

1. An information processing apparatus comprising:
one or more processors; and
one or more memories that store a command executed by the one or more processors,
wherein the one or more processors are configured to:
acquire a text;
classify attributes of information described in each fixed unit of the text;
analyze the text for each of same classifications based on a result of the classification to extract terms from a set of fixed units for each of the same classifications;
acquire a relationship between the extracted terms in the set of fixed units for each of the same classifications; and
output a structured result of the text according to the extracted terms and the relationship between the extracted terms for the set of fixed units for each of the same classifications.

2. The information processing apparatus according to claim 1,
wherein the each fixed unit is any one of a sentence unit, a phrase unit, a word unit, or a character unit.

3. The information processing apparatus according to claim 1,
wherein the text is a medical text.

4. The information processing apparatus according to claim 1,
wherein a classification item of the information includes one or more of a human body part, an organ, a type of a disease, a type of a medical process, and a presence or absence of a disease.

5. The information processing apparatus according to claim 4,
wherein the type of the medical process includes at least one of findings, diagnosis, or past comparison.

6. The information processing apparatus according to claim 1,
wherein the term extraction includes acquisition of a term expression and determination of a term type.

7. The information processing apparatus according to claim 1,
wherein the terms are extracted by using a prediction model subjected to machine learning in advance.

8. The information processing apparatus according to claim 1,
wherein at least one of the extracted terms or the relationship between the extracted terms is acquired by using a prediction model subjected to machine learning in advance.

9. The information processing apparatus according to claim 8,
wherein different prediction models are used depending on the result of the classification.

10. The information processing apparatus according to claim 7,
wherein the text for each of the same classifications and classification information of the same classification are used as an input to the prediction model.

11. The information processing apparatus according to claim 1, further comprising:
an input apparatus that receives an input of the text; and
a display apparatus that displays the result of the analysis.

12. The information processing apparatus according to claim 1,
wherein the one or more processors are configured to:
save the result of the classification, and
perform processing of displaying the result of the classification in an identifiable manner in a case where the acquired text is displayed.

13. The information processing apparatus according to claim 1, wherein the one or more processors determine a type of medical process and a type of organ for the each fixed unit of the text as the attributes of information described in the each fixed unit of the text.

14. The information processing apparatus according to claim 1, wherein the one or more processors analyze the text based on a type of the organ to extract the terms from a set of fixed units for each same type of organ.

15. The information processing apparatus according to claim 1, wherein the one or more processors acquire the relationship between the extracted terms in the set of fixed units having a same type of organ.

16. An information processing method executed by one or more processors, the information processing method comprising:
by the one or more processors,
acquiring a text;
classifying attributes of information described in each fixed unit of the text;
analyzing the text for each of same classifications based on a result of the classification to extract terms from a set of fixed units for each of the same classifications;
acquiring a relationship between the extracted terms in the set of fixed units for each of the same classifications; and
outputting a structured result of the text according to the extracted terms and the relationship between the extracted terms for the set of fixed units for each of the same classifications.

17. A non-transitory, computer-readable tangible recording medium which records thereon a program for causing, when read by a computer, the computer to realize:
acquire a text;
classify attributes of information described in each fixed unit of the text;
analyze the text for each of same classifications based on a result of the classification to extract terms from a set of fixed units for each of the same classifications;
acquire a relationship between the extracted terms in the set of fixed units for each of the same classifications; and
output a structured result of the text according to the extracted terms and the relationship between the extracted terms for the set of fixed units for each of the same classifications.

\* \* \* \* \*